US 8,097,041 B2

(12) United States Patent
Barbosa (10) Patent No.: US 8,097,041 B2
(45) Date of Patent: Jan. 17, 2012

(54) INFRA-ORBITAL IMPLANT

(75) Inventor: Karen S. Barbosa, Huntington, NY (US)

(73) Assignee: Epitera Solutions, Inc., Highland Heights, OH (US)

( * ) Notice: Subject to any disclaimer, the term of this patent is extended or adjusted under 35 U.S.C. 154(b) by 363 days.

(21) Appl. No.: 12/364,495

(22) Filed: Feb. 2, 2009

(65) Prior Publication Data

US 2009/0198335 A1 Aug. 6, 2009

Related U.S. Application Data

(60) Provisional application No. 61/063,041, filed on Jan. 31, 2008.

(51) Int. Cl.
*A61F 2/02* (2006.01)
(52) U.S. Cl. .................................................. 623/23.72
(58) Field of Classification Search ................... 623/4.1, 623/11.11, 15.11, 15.12, 17.18, 17.19, 23.53, 623/23.54, 23.58, 23.59, 23.72–23.76
See application file for complete search history.

(56) References Cited

U.S. PATENT DOCUMENTS

| 3,953,566 | A | * | 4/1976 | Gore | 264/505 |
| 3,992,725 | A | | 11/1976 | Homsy | |
| 4,790,849 | A | * | 12/1988 | Terino | 623/17.18 |
| 5,421,831 | A | | 6/1995 | Giampapa | |
| 5,876,447 | A | * | 3/1999 | Arnett | 623/17.18 |
| 6,277,150 | B1 | * | 8/2001 | Crawley et al. | 623/17.18 |
| 7,108,718 | B1 | | 9/2006 | Li et al. | |
| 2002/0007294 | A1 | * | 1/2002 | Bradbury et al. | 705/7 |

* cited by examiner

*Primary Examiner* — David Isabella
*Assistant Examiner* — Suba Ganesan
(74) *Attorney, Agent, or Firm* — Fay Sharpe LLP (57) ABSTRACT

An infra-orbital implant is provided for surgically altering the appearance of an infra-orbital region of an associated human eye. The implant includes a body made from a biocompatible material adapted for use with human tissue. The body includes an anterior surface and a posterior surface. The anterior surface of the body includes a skin tone correction surface. The skin tone correction surface of the infra-orbital implant cooperates with the overlying skin to correct a skin tone of the infra-orbital region when the implant is introduced beneath the skin portion of the infra-orbital region of the associated human eye.

5 Claims, 11 Drawing Sheets

INFRA-ORBITAL IMPLANT

A claim for domestic priority is made herein under 35 U.S.C. §119(e) to U.S. Provisional App. Ser. No. 61/063,041 filed on Jan. 31, 2008, the entire disclosure of which is incorporated herein by reference.

BACKGROUND

The present application relates to the general field of blepharoplasty. It finds particular application to medical implants used in connection with the eye, eyelids, and/or surrounding structures and will be described with reference thereto. However, other applications are also contemplated.

A common problem or condition affecting individuals of all ages is the presence of dark circles under the eyes, also referred to as "sunken eyes." Generally, these dark circles can make an individual look older than they really are, fatigued and/or upset. A variety of factors can be tied to the cause of darkness under the eyes. These include genetics, the natural aging process, allergies, exposure to ultraviolet light, fatigue, etc. In addition, darkness under the eyes can result from the thinning of the skin underlying the eyes, thinning of the infra orbital rim and/or loss of, shifting or pseudo-herniation of the fat deposits or fat pads near the infra-orbital rim and/or orbital septum.

Thinning of the skin allows for the underlying vessels, veins, muscle, or other dark hue structures (all of which are typically dark red or blue) to influence, discolor, or give the appearance of darkening the tone of the overlying thinning skin area. Thinning of the infra-orbital rim can also cause the appearance of dark circles under the eyes but in a different manner. When the infra-orbital rim thins or shrinks, the overlying skin, fat, muscles, vessels, etc. tend to recede or move in a posterior direction together with the infra-orbital rim creating a depressed region beneath or about the eye. Light directed downward from an elevated perspective would cause a shadow to be cast in the depressed region thus giving the appearance of a darker infra-orbital skin region. An outward bulging portion under the eye due to pseudo-herniation of a fat deposit, fat pad, or orbital septum can also result in shadow formation. An outward bulge under the eye or infra-orbital region would also cause a shadow to be cast under certain lighting conditions giving the appearance of dark circles due to the change in relative surface elevation between the bulging skin portion and the surrounding healthy skin regions adjacent the eye and/or the cheek. Just as a mountain eclipses sunlight from an oppositely disposed valley, the bulging skin portion can also eclipse light, causing a shadow to be cast to the adjacent healthy skin portions thus giving the appearance of dark circles. In still other cases, darkness under the eyes may be the result of skin hyper-pigmentation.

The current procedures for correcting or treating dark circles typically involve fat grafting, collagen injections, chemical treatments, lotions, make-up and/or chemical peels. However, these techniques provide only marginal results and must usually be repeated often in order to achieve the desired effect. While a surgical procedure involving fat grafting can be done to remove excess fat cells from one part of the body and transplant them to the depressed or sunken portion of the infra-orbital region of the eye, any positive results achieved from such a procedure rarely last more than a few months since they are eventually reabsorbed by the body. Collagen injections similarly provide only a short term benefit. Moreover, there is always the risk that the body will reject the fat graft or collagen which may also result in an infection and/or inflammation of the treated site.

For at least these reasons, a need exists to provide a solution for more permanently correcting the condition of dark circles while overcoming the aforementioned problems and others.

SUMMARY

According to one aspect of the present invention, an infra-orbital implant for surgically altering the appearance of an infra-orbital region of an associated human eye is provided. The implant includes a body made from a biocompatible material adapted for use with human tissue. The body includes an anterior surface and a posterior surface. The anterior surface of the body includes a skin tone correction surface. The skin tone correction surface of the infra-orbital implant cooperates with the overlying skin to correct a skin tone of the infra-orbital region when the implant is introduced beneath the skin portion of the infra-orbital region of the associated human eye.

According to another aspect of the present invention, an infra-orbital implant system is provided for surgically altering the appearance of an infra-orbital region of an associated human eye. The implant system includes a first implant having a body made from a pliable yet resilient biocompatible material adapted for use with human tissue. A posterior ridge is disposed on the posterior surface of the first implant and extending in a generally posterior or rearward direction. The posterior ridge cooperates with an infra-orbital rim of the associated human eye to advance an anterior tissue portion overlying the first implant in a generally anterior direction when the implant is introduced beneath the skin portion of the infra-orbital region of the associated human eye.

According to yet another aspect of the present invention, a method of implanting an infra-orbital implant for improving cosmesis of an infra-orbital region of an associated human eye is provided. An infra-orbital implant is provided including a body made from a biocompatible material adapted for use with human tissue. The body includes an anterior surface and a posterior surface. An incision below a hairline of a lower eyelid of the associated human eye is created. The infra-orbital implant is inserted via the incision beneath the skin in the infra-orbital region of the associated human eye. The infra-orbital implant is oriented and the incision is closed.

BRIEF DESCRIPTION OF THE DRAWINGS

The invention may take form in various components and arrangements of components and various steps and arrangement of steps. The drawings are only for purposes of illustrating various embodiments of the invention and are not to be construed as limiting the invention.

DETAILED DESCRIPTION

Figure 1:
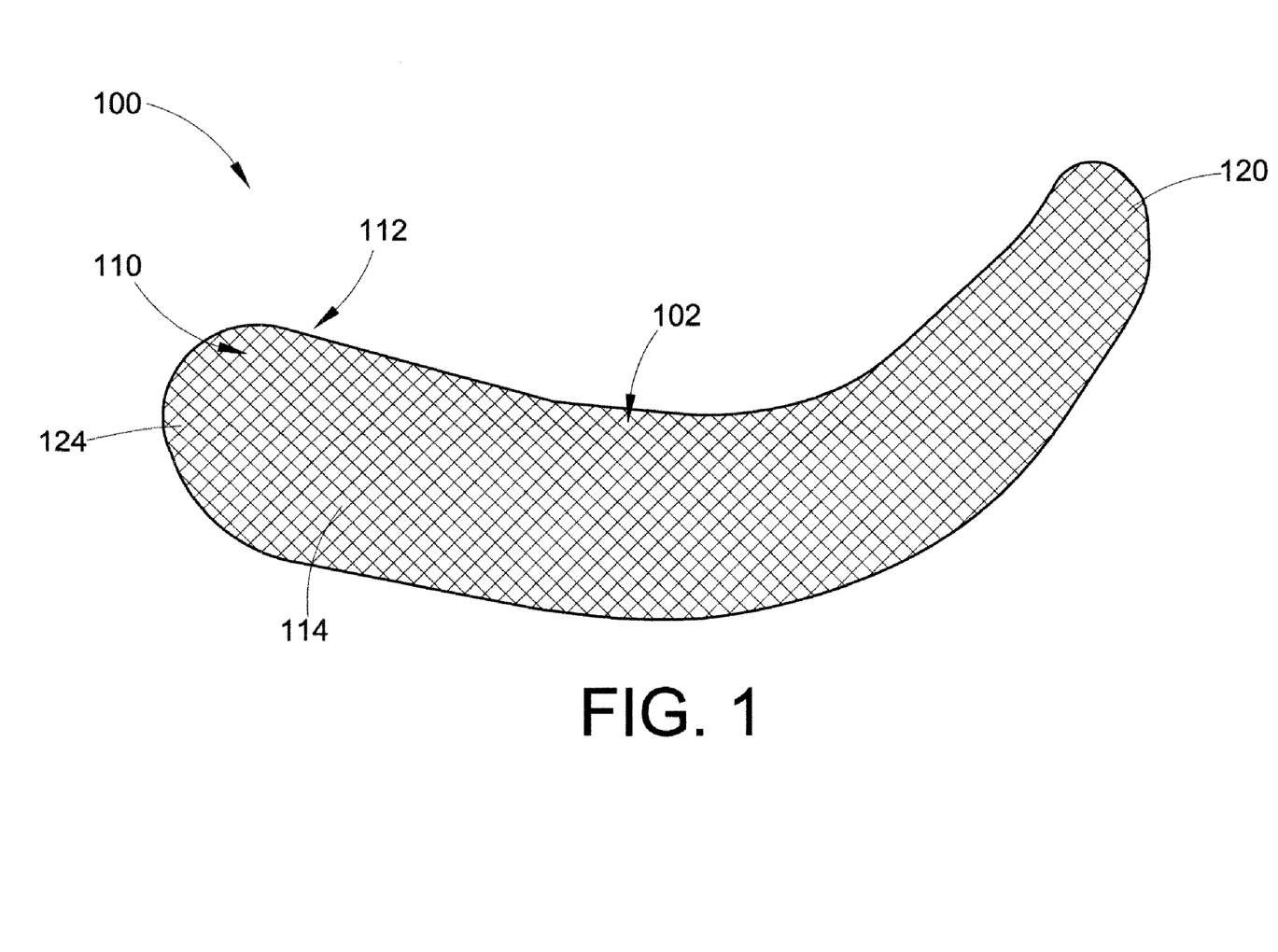
FIG. 1 is a perspective view of a first embodiment of an infra-orbital implant according to the present invention.

With reference to FIG. 1, a first embodiment of an infra-orbital implant 100 is shown. As illustrated, the implant 100 generally includes a body 102 having an anterior surface 110 and a posterior surface 112. The body 102 may be formed in one or more layers such that the anterior surface 110 may include different material properties than the posterior surface 112. For instance, the anterior surface 110 may include a relatively smooth and/or a semi-reflective surface. Utilizing a semi-reflective surface can aid in further negating the darkened circle A (FIG. 10) or sunken eye appearance by reflecting a greater portion of light surrounding the eye. Moreover, the anterior surface 110 or body 102 can be colored so as to complement an existing skin tone or hue of the skin proximal to the implant site. Alternately, the anterior surface 110 or body 102 can be colored differently so as to counteract or neutralize the existing skin tone if the existing skin tone proximal to the implant site is discolored or otherwise not preferred. The portion of the implant containing the various surface characteristics which affect the transmission, filtering, and or reflectivity of the light and which is responsible for the resulting changes in skin tone, can be referred to as a skin tone correction surface or layer. In addition, the posterior surface 112 or body 102 may include a surface texture, roughness, or porosity so as to promote tissue in-growth. As illustrated in FIG. 1, the body 102 of the implant 100 may include a fine woven graft or mesh 114 which allows the implant 100 to be resilient, yet extremely pliable while allowing for tissue in-growth.

The implant 100 may be formed from any material that is biocompatible. By way of example only, the implant 100 may be formed from a polymer or an elastomer based material such as Gortex or expanded polytetrafluoroethylene (ePTFE). Similarly, Dacron, silicone, synthetic biogenerated graft, a porcine graft, a human graft or any other material that carries a low risk of tissue rejection after introduction to the human body can be used.

Figure 2:
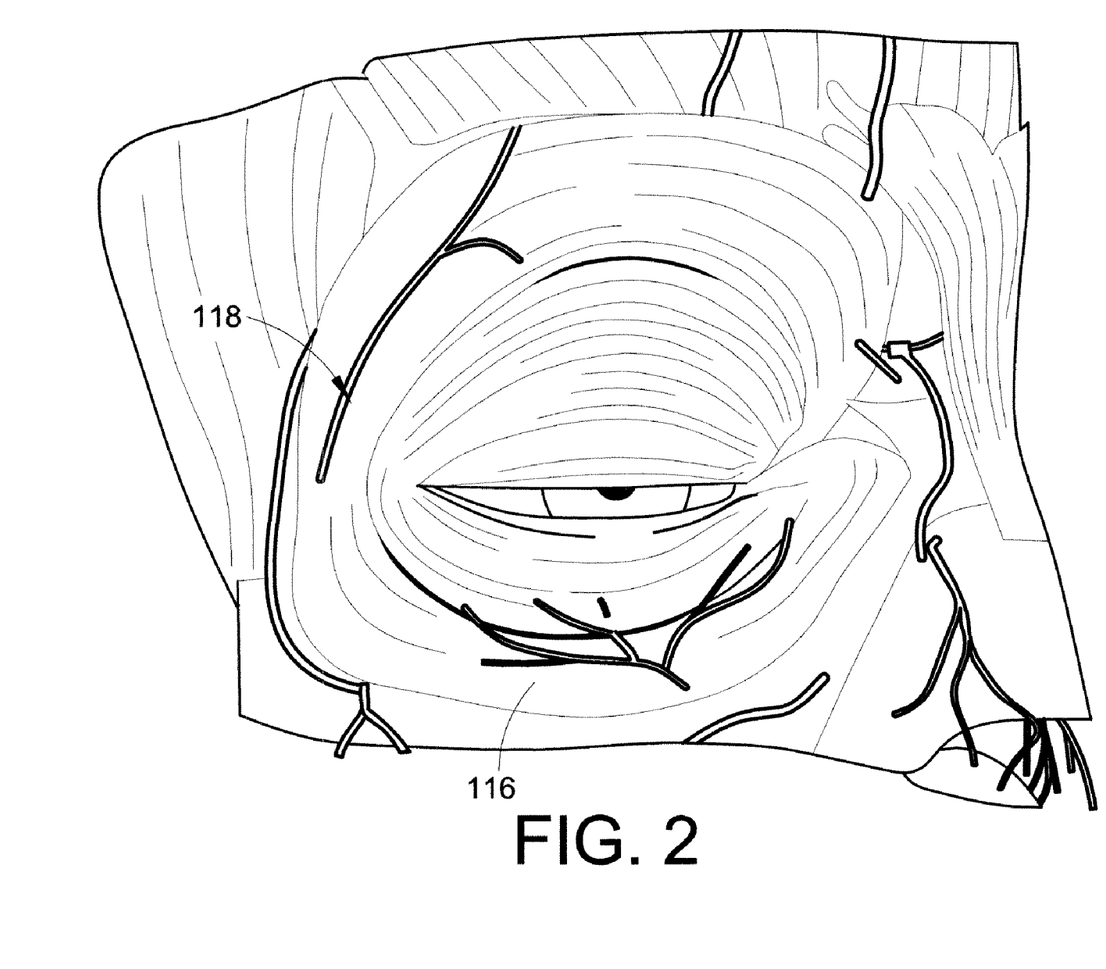
FIG. 2 is a perspective view of a muscular and vascular structure surrounding an orbital region of a human eye.
Figure 3:
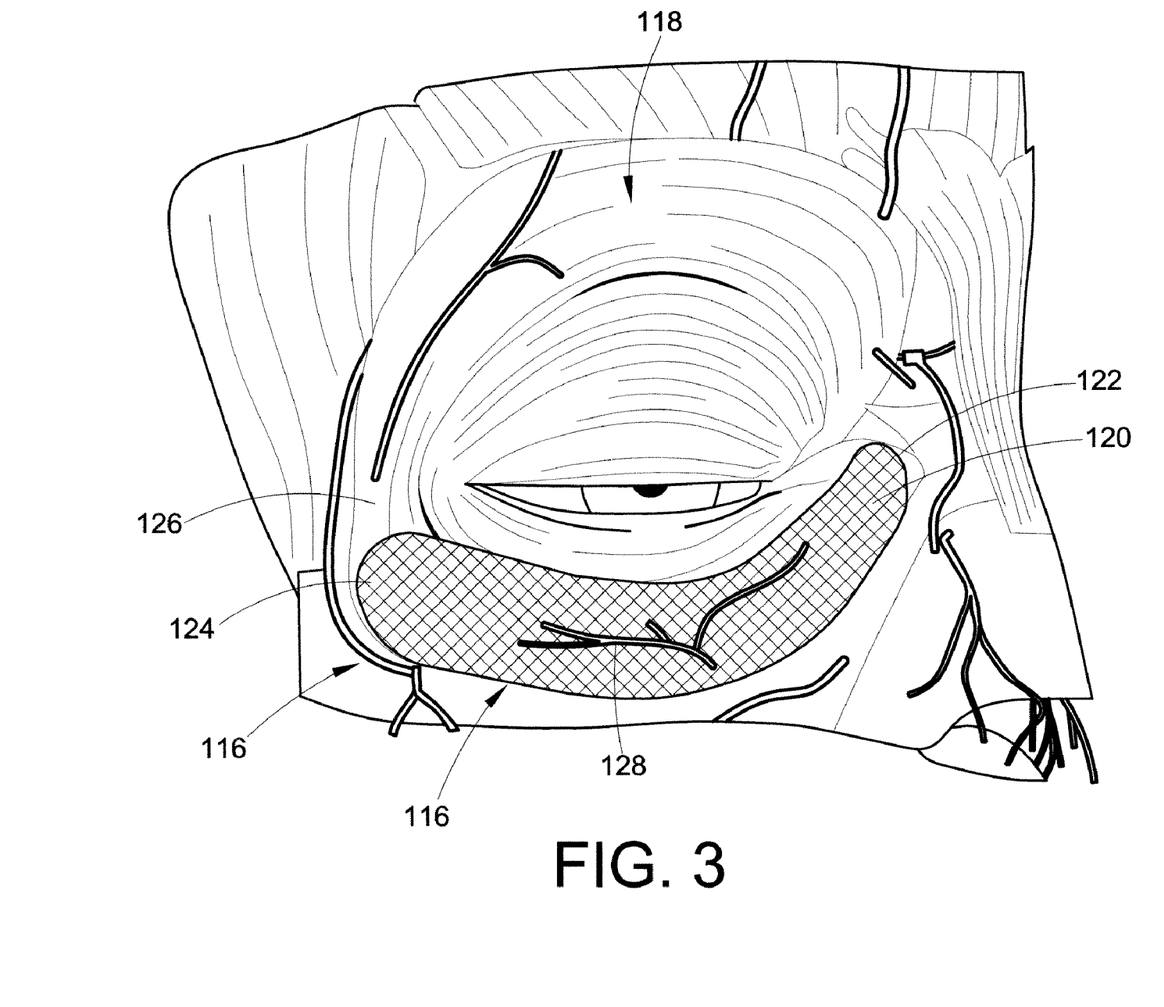
FIG. 3 is a perspective view of the human eye of FIG. 2 illustrating the placement of the infra-orbital implant of FIG. 1.

With reference to FIGS. 1-3, the infra-orbital implant 100 is generally intended to be used in an infra-orbital region 116 of a human eye 118. A first end 120 of the implant 100 can be oriented near a medial portion of the eye 122, while a second end 124 of the implant 100 is oriented towards a lateral or outer portion of the eye 126. As will be discussed in greater detail below, the implant 100 can be generally placed between the orbicularis oculi muscle of the eye and the skin located in the affected sunken or darkened circle portion within the infra-orbital region of the eye. In this general vicinity, an infra-orbital vascular structure including a plurality of blood vessels 128 is present within the infra-orbital region 116 of the eye 118.

Figure 4:
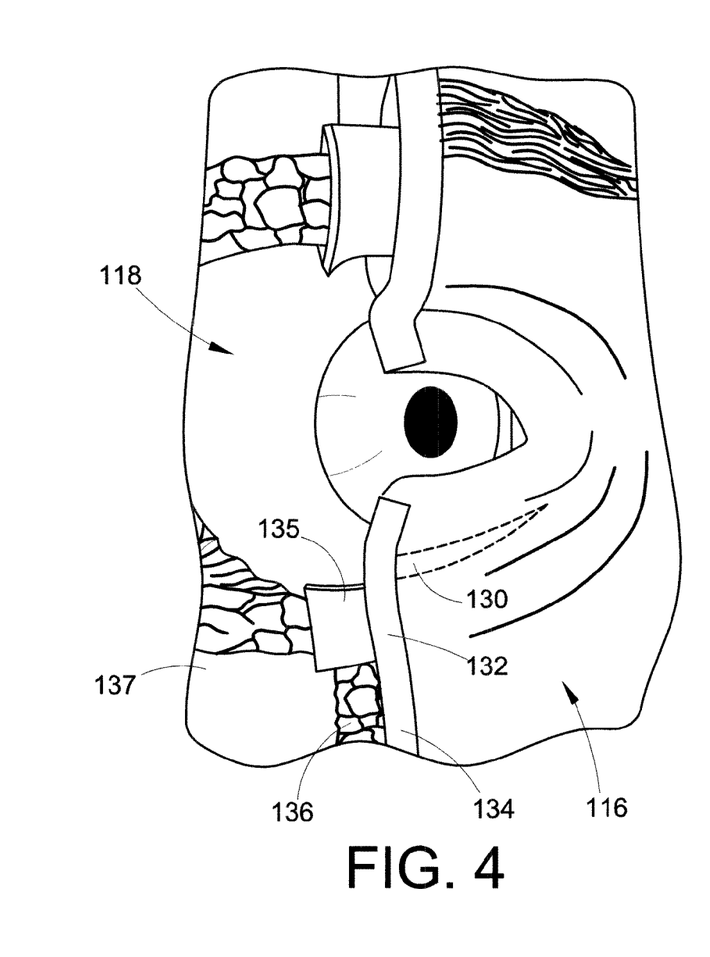
FIG. 4 is a perspective view in a partial sagittal section of the human eye of FIG. 2.
Figure 6:
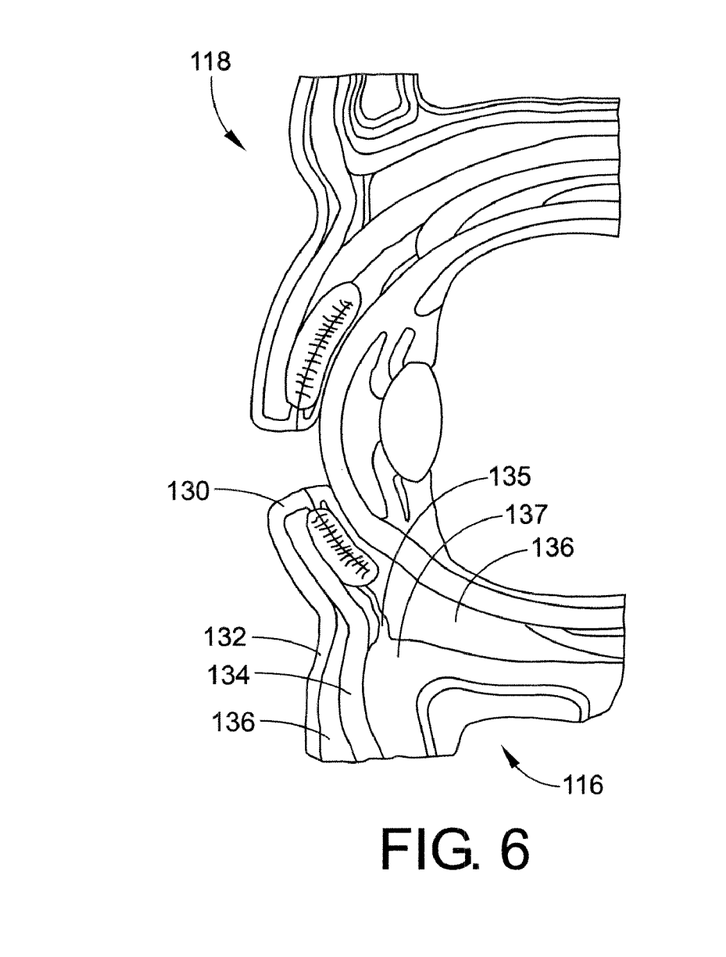
FIG. 6 is a partial sagittal view of a healthy human eye.
Figure 10:
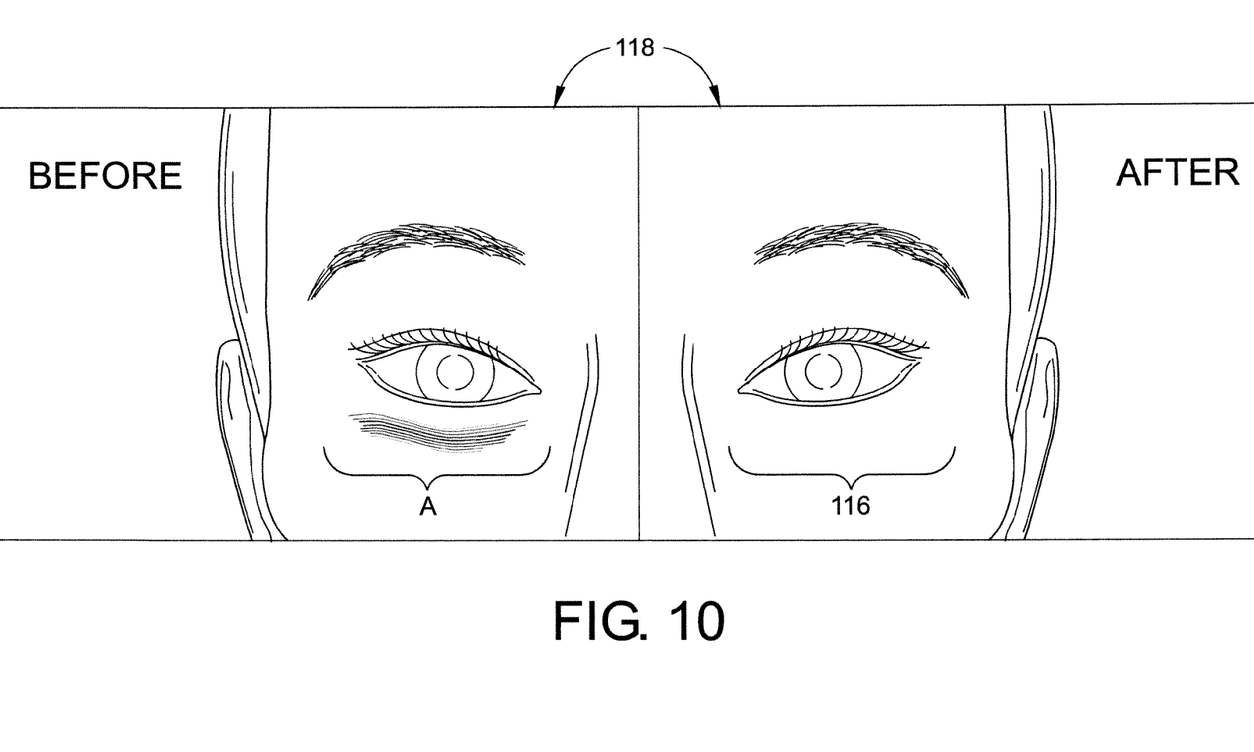
FIG. 10 is a front or anterior view of a right and a left eye of an individual illustrating a before state prior to the infra-orbital implant procedure and an after state illustrating the results of the infra-orbital implant procedure, respectively.

With reference to FIGS. 4 and 6, the relevant structures surrounding the eye 118 and infra-orbital region 116 are illustrated in a healthy human eye. In particular the lower eyelid 130 is shown in cross section and illustrates an infra-orbital skin portion 132, an infra-orbital orbicularis oculi muscle 134, an orbital septum 135, one or more infra-orbital fat deposits or fat pads 136, and an infra-orbital rim 137 are illustrated. As described previously, the fat deposits 136 in and/or near the infra-orbital rim tend to thin, "shrink", or shift with age causing the sunken or dark circle area A (FIG. 10). In addition, the skin 132 may also begin to thin with age and become more transparent thereby revealing the darker underlying vascular and/or muscular structures further causing the darkened circle appearance.

Figure 7:
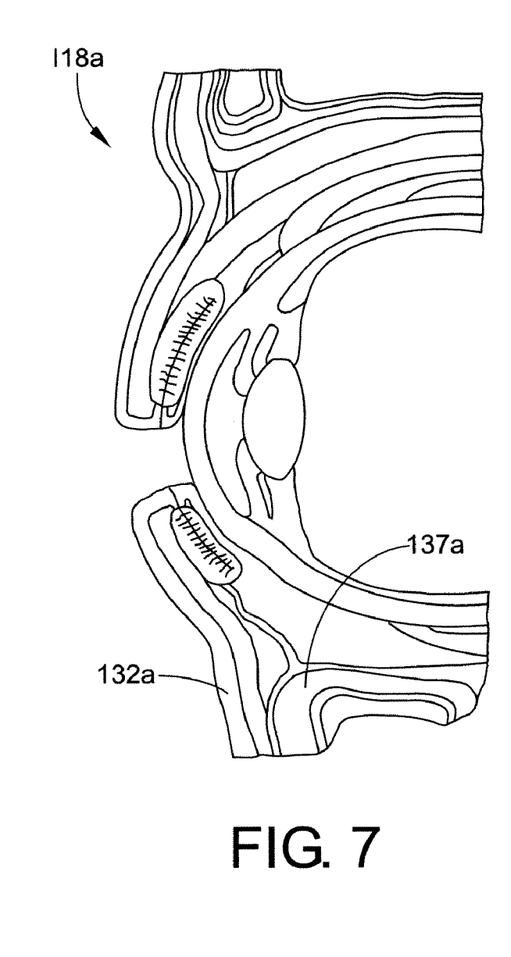
FIG. 7 is a partial sagittal view of a human eye afflicted with thinning skin and or a thinning infra-orbital rim.

With reference to FIG. 7, a human eye 118a afflicted with a thinning skin area 132a and a thinning infra-orbital rim 137a is shown. By comparing FIGS. 6 and 7 it is readily apparent that the infra-orbital rim has receded or shrunk such that a depressed area adjacent the thinning skin area 132a is created. The infra-orbital rim 137a appears to have shifted into a lower and more posterior position. As stated previously, at least one objective of the instant invention is to restore the skin 137a below the lower eye lid to its original position (as shown by rim 137 in FIG. 6) through the addition or introduction of one or more suitable infra-orbital implant(s).

Figure 8:
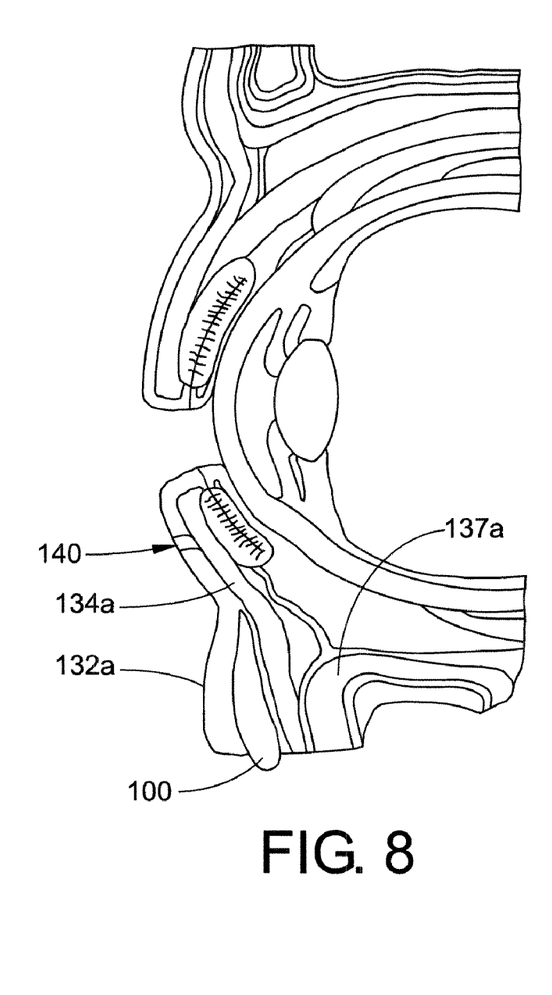
FIG. 8 is a partial sagittal view of the afflicted human eye of FIG. 7 illustrating the placement of the first embodiment of the infra-orbital implant beneath the skin and anterior of the orbicularis oculi.

In order to raise the depressed or sunken region adjacent the thinning skin portion 132a (FIG. 7), A (FIG. 10) and to mask or prevent the darker hues of the underlying structures from being visible, the infra-orbital implant 100 can be inserted between the skin portion 132 and the muscle 134 as illustrated in FIG. 8. As illustrated in FIG. 8, the orbital implant 100 may be opaque, i.e. having a very low light transmissive property, thus preventing the dark underlying muscular/vascular structures from being visible through the skin. Moreover, the implant could include a reflective property and or a particular hue that effectively reflects light and/or cancels out the undesired hue of the overlying skin. In addition, the implant 100 may act as a filler compensating for the fat loss of the surrounding fat pads, thinning of the skin 132, and/or the thinning of the infra-orbital rim. It should be noted that while the implant 100 is illustrated as being between the skin 132 and the muscle 134 other locations such as within or beneath the muscle 134 are also contemplated.

Figure 9:
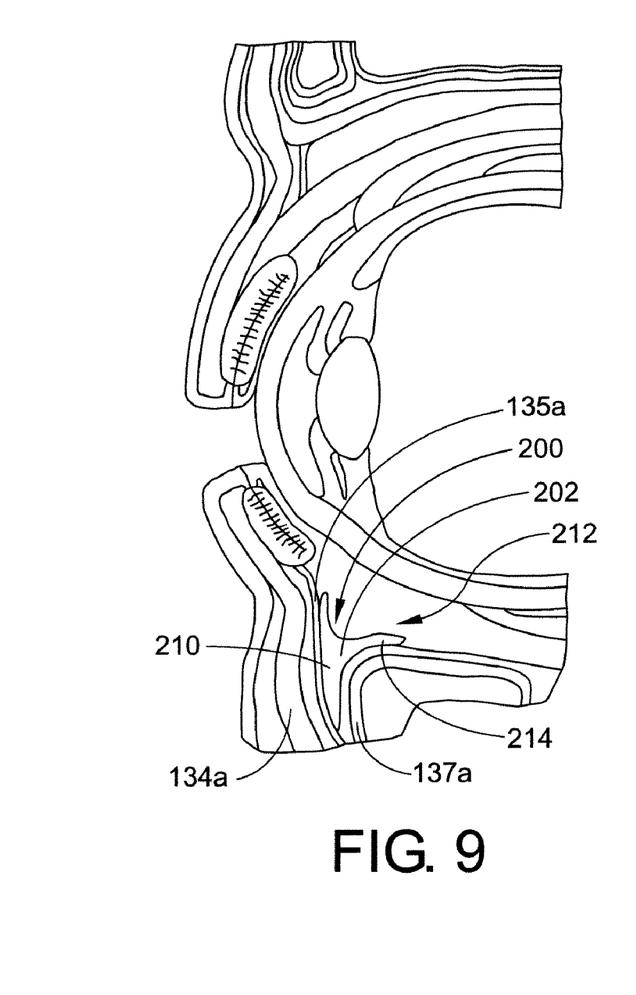
FIG. 9 is a partial sagittal view of the afflicted human eye of FIG. 7 illustrating the placement of a second embodiment of an infra-orbital implant posterior to the orbital septum and anterior to the infra-orbital rim.
Figure 9A:
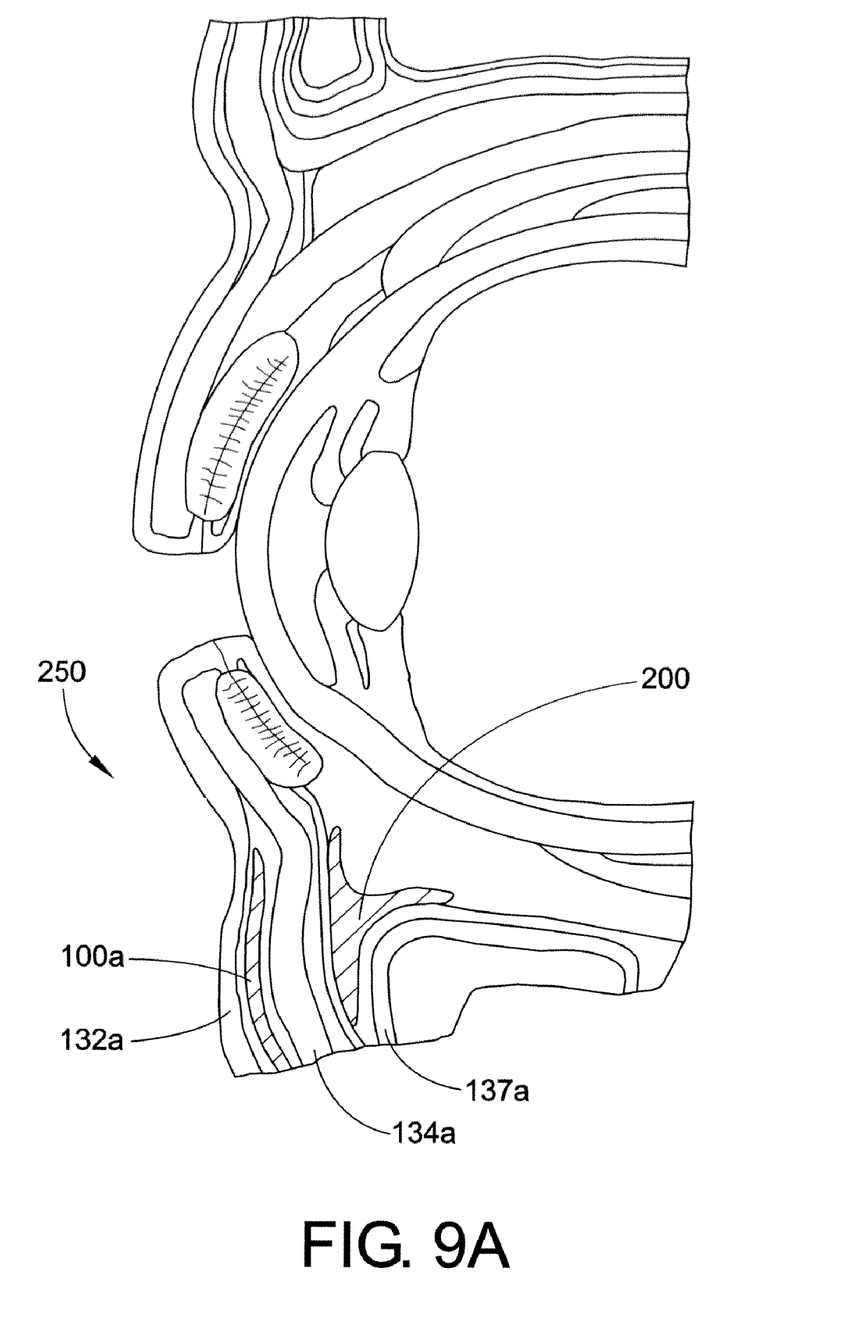
FIG. 9A is a partial sagittal view of the afflicted human eye of FIG. 7 illustrating the placement of one embodiment of an infra-orbital implant system including a first infra-orbital implant posterior to the orbital septum and anterior to the infra-orbital rim and a second infra-orbital implant just beneath the afflicted skin portion.

Furthermore, and with reference to FIG. 9A, a system 250 of one or more implants (100a, 200) could be used in combination. For example, where dark circle or shadow formation is the primary result of a depressed infra-orbital region, two implants could be used. A first implant 200 (as discussed in greater detail below with reference to FIG. 9) can be placed behind the muscle 134a and anterior to the orbital rim 137a for the purpose of correcting the depression by raising the overlying structures. A second implant 100a, similar to implant 100 (FIG. 8) of the first embodiment, that is relatively thin and includes the appropriate light transmissive and/or reflective properties can then be placed just beneath the skin to correct any undesired hues in the overlying skin 132a. By comparison, if only one large depression filling implant were to be introduced just beneath the skin, it is possible that necrosis of the overlying skin or adjacent structures could occur. Such necrosis could be induced due to the interruption or lack of circulation. Moreover, the potential exists for scarring, scar tissue formation, or contracture to occur. Scarring could further lead to excessive or undesired movement of the implant particularly if a porous/tissue in-growth design is implemented. Further still, scarring or contracture could result in the dropping of the lower eye lid. Thus, using one implant to correct light responsive properties and one beneath the muscle to correct depth would generally be preferred. It should be noted that where one or more implants are used in conjunction to correct the aforementioned problems, any combination of implants having various surface features could be used (i.e., some could include porous features so as to promote in-growth and vascularization to the overlying structures and others could be smooth and thin so as to minimize the growth of scar tissue and the likelihood of tissue rejection).

Now with reference to FIG. 9, a second embodiment of an infra-orbital implant 200 is illustrated and is particularly suited for placement between the infra-orbital rim 137a and the orbicularis oculi muscle 134a. As with the first embodiment, the infra-orbital implant 200 includes a body 202 having an anterior surface 210 and a posterior surface 212. The intended goal of the implant 200 is to advance the overlying anterior tissue so as to restore the thinning skin area and reduced the appearance of "sunken" eyes and or dark circles by filling the void created primarily by the shrinking or receding infra-orbital rim 137a. To do so, the anterior surface of the of the implant 200 is generally smooth so as not to irritate the orbital septum and or muscle 134a. The body portion 202 can also be trimmed or fitted to provide the correct amount of fill. Lastly, a rearwardly projecting posterior ridge 214 can be contoured to rest or be secured to or adjacent the infra-orbital rim. The posterior ridge also extends generally laterally along the implant from a medial end to an outer or lateral end. Naturally, the width of the ridge can also be fitted, trimmed, or curved to best accommodate the infra-orbital rim 137a.

Figure 5:
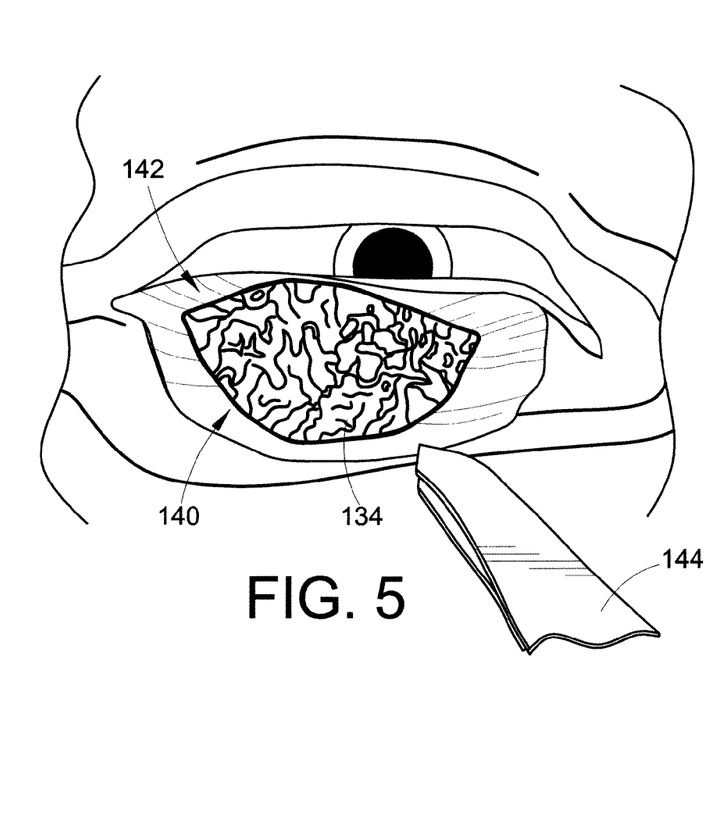
FIG. 5 is a front or anterior view of the eye illustrating an incision made in the lower eyelid to reveal the underlying tissues and/or orbital septum of the eye.

With reference to FIG. 5 and continued reference to FIG. 8, one possible technique for inserting the implant 100 is an infra-ciliary method which involves creating an incision 140 just beneath the hairline of the lower eyelid 142. Using a pair of forceps 144, a surgeon may retract the lower portion of the incision to expose the underlying muscle 134, 134a. At this point, the implant can be inserted through the opening of the incision, placed beneath the skin in the infra-orbital region, and oriented for optimal cosmesis. Thereafter, the surgeon may use absorbable sutures to secure the implant in place to the underlying or surrounding tissue regions and lastly close the incision 140. It should be noted that the implant could also be inserted under the skin in the infra-orbital region via an incision in the conjunctiva, i.e. through the inner surface of the lower eye lid. By performing the implantation procedure via transconjuctival insertion, scarring that might otherwise be visible will be entirely concealed by the eye lid. A similar percutaneous or transconjuctival implantation procedure can be used to insert the second embodiment of the implant 200 (FIG. 9). However, introduction of the implant 200 will likely require a division of the orbital septum 135a and or periosteum from the infra-orbital rim 137a.

As noted previously, the implant may include a variety of surface features, such as a grid-like mesh, woven or a randomly porous body, any of which can promote tissue in-growth with the implant. If such in-growth surface features or implants are utilized, absorbable or dissolvable sutures may be used during the procedure to temporarily secure the implant until adequate tissue in-growth has occurred. Furthermore, utilizing an implant with a porous body can greatly increase the success of the procedure by allowing the underlying vascular structure to permeate the implant and continue to supply blood to the skin, muscle or other tissue structures overlying the implant.

It should also be noted, that the implant can be manufactured as a sheet material, available in varying thicknesses, and altered in shape or geometry as necessary by the surgeon prior to or during the procedure so as to best accommodate each particular patient. On the other hand, and as illustrated in FIG. 1, the implant 100 can be manufactured or pre-cut into a generally semi-circular or crescent shape. Doing so, will ensure symmetry when both left and right eyes are to receive an implant.

In addition, the thickness of the implant can be varied depending on the amount of volume required to be filled in order to create a generally even cosmetic contour or smooth transition between the affected infra-orbital skin 132a (FIG. 7) or the dark circle region A (FIG. 10) and the skin that is adjacent or proximal to it, such as the skin covering the cheek. Typically, the thickness of the implant may range from a few hundred microns in thickness to a few millimeters.

It should be noted that varying the thickness of any of the disclosed embodiments of the infra-orbital implant can be used to treat a variety of peri-orbital cosmetic problems such as creases in the skin, fat protrusion, tear trough/depression in the infra-orbital region, and dark circles. Creases in the skin can be addressed by increasing the thickness of the implant used by filling volume beneath the skin thus resulting in decreased skin laxity. Fat protrusion can be addressed by using the implant to restrict fat from prolapsing anteriorly. Tear trough/depression in the infra-orbital region is addressed by restoring the infra-orbital volume such that the overlying skin is even or flush. Dark circles are also addressed by ameliorating any combination of the aforementioned cosmetic problems.

Now with reference to FIG. 10, a side by side comparison of a before or pre-operative state and an after or post-operative state of the eye 118 is shown. As illustrated, in the before state, the darkened circle region A includes a localized darkened region which also appears to be sunken due to the thinning of the surrounding skin and/or loss of the fatty tissue surrounding the infra-orbital region. Once the implantation procedure has been performed and the patient has recovered, the infra-orbital region 116, as illustrated on the right hand side of FIG. 10, will appear closer in color and more evenly contoured as compared to the adjacent skin surrounding the infra-orbital region.

Figure 11:
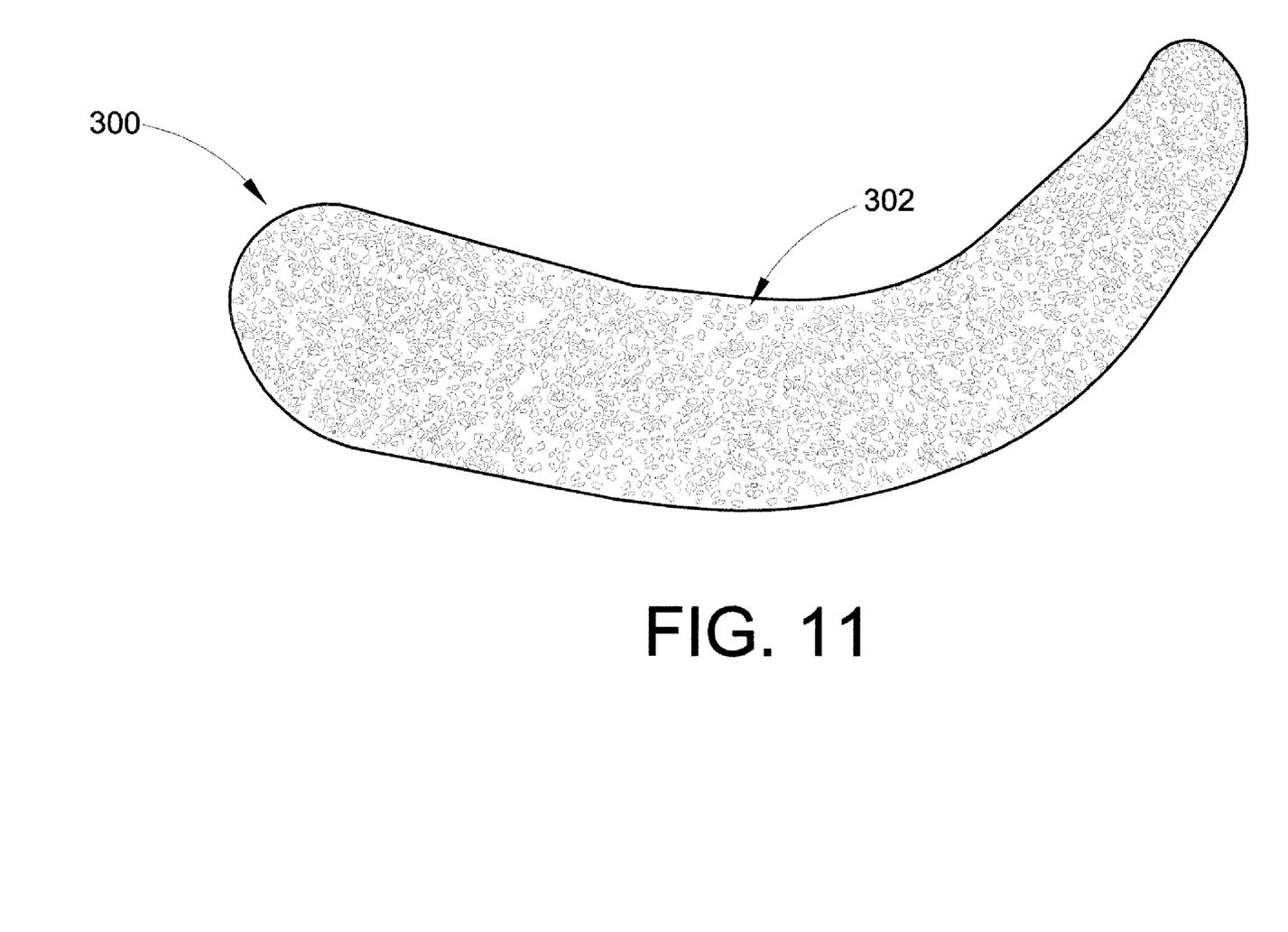
FIG. 11 is a perspective view of another embodiment of an infra-orbital implant including a porous surface, according to the present invention.
Figure 12:
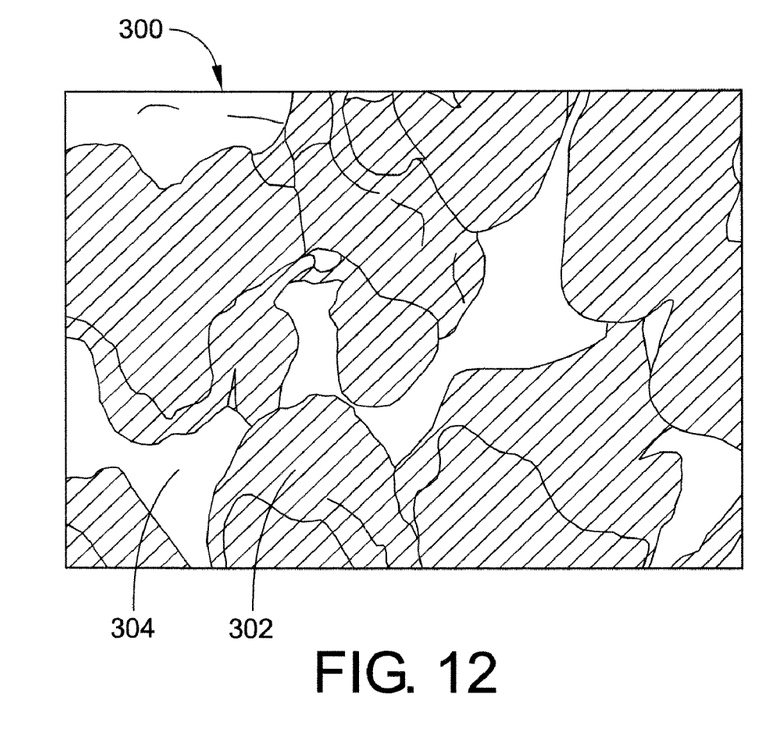
FIG. 12 is an enlarged cross section view of the porous surface of the infra-orbital implant of FIG. 11.
Figure 13:
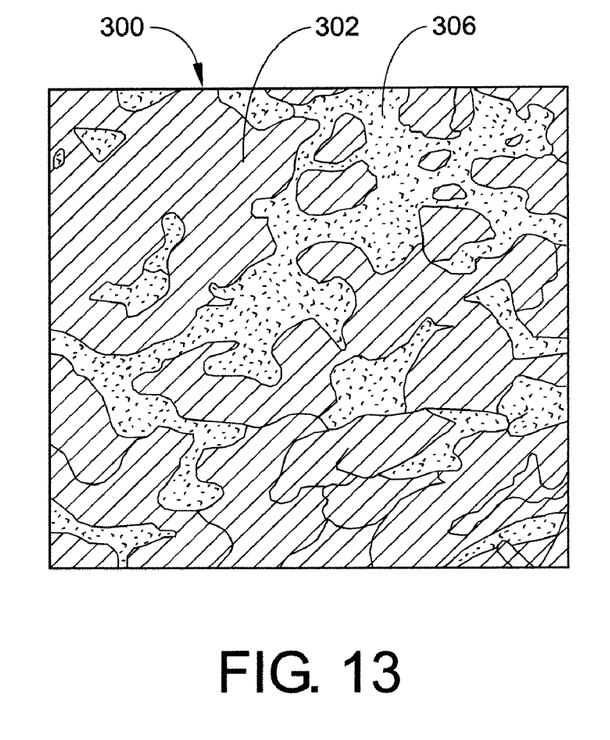
FIG. 13 is an enlarged cross section view of the infra-orbital implant of FIG. 11 after implantation illustrating tissue in-growth into the implant.

With reference to FIGS. 11 through 13, an enlarged cross section of an alternate embodiment of a bio-compatible infra-orbital implant 300 is shown illustrating the body or substrate 302 of the implant 300. As is illustrated in FIG. 12 and prior to implantation, the substrate 302 includes voids or porous features 304 that permit for tissue in-growth. In addition, the non-porous portions of the substrate 302 are irregular and random in surface geometry. Such irregularity generally provides better adhesion between the surrounding ingrown tissue and the implant 300. After implantation and adequate recovery, substantial tissue in-growth can be achieved. With reference to FIG. 13, the implant 300 is now shown in situ and entirely surrounded by in-grown tissue 306. As illustrated, healthy tissue 306 will readily adapt and grow into the substrate 302 of the implant 300.

Figure 14:
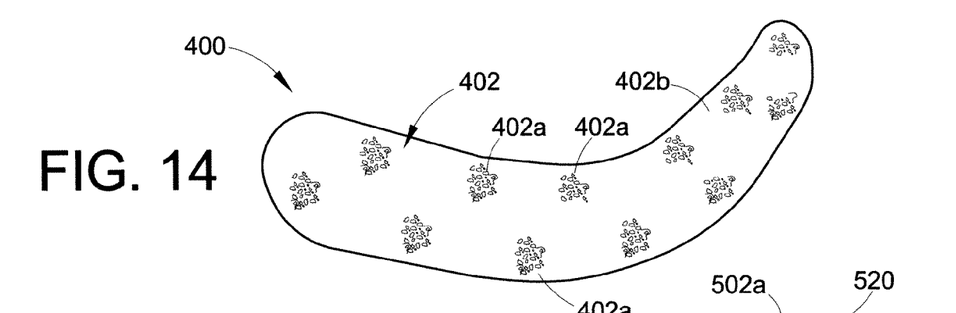
FIG. 14 is a perspective view of yet another embodiment of an infra-orbital implant having a body which includes a semi-porous and semi-smooth region, according to the present invention.

With reference to FIG. 14, another embodiment of a biocompatible infra-orbital implant 400 is shown illustrating a body 402 including voids or porous regions 402a (similar to the porous features 304 depicted in the implant 300 of FIG. 11). The porous regions 402a may be dispersed evenly or randomly throughout the body 402 and may be placed either on an anterior or posterior surface or may extend from the anterior surface through the body 402 and towards the posterior surface. The overall surface area of the implant that is porous can be between 20% to 70%. The areas between the porous regions 402a may include smooth regions 402b. One advantage for using implant 400 is that the amount of tissue in-growth can be limited by the quantity or total area of porous regions. This can be beneficial in reducing adverse effects of tissue in growth such as scarring, discoloration, or necrosis of the overlying/underlying tissue structures.

Figures 15, 16:
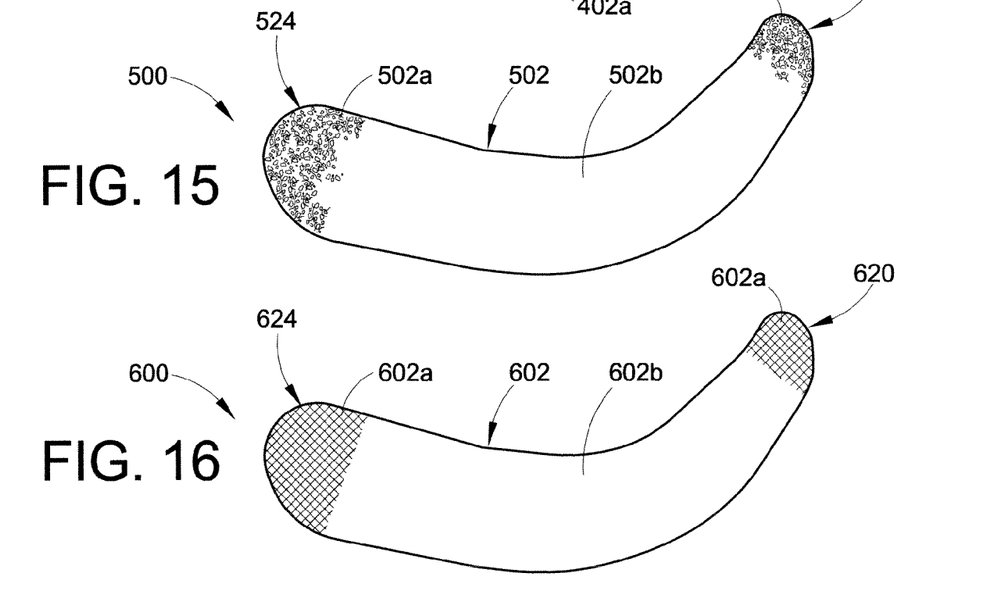
FIG. 15 is a perspective view of yet another embodiment of an infra-orbital implant having a body which includes porous end regions and a smooth central region, according to the present invention.
FIG. 16 is a perspective view of yet another embodiment of an infra-orbital implant having a body which includes mesh end regions and a smooth central region, according to the present invention.

With reference to FIG. 15, yet another embodiment of a bio-compatible infra-orbital implant 500 is shown illustrating a body portion 502 having porous regions 502a at the ends of the implant which are separated by a smooth central non-porous region 502b. As illustrated in FIG. 15, a porous region 502a may be located at the medial end 520 of the implant 500 and another porous region may be located at a lateral end 524. Once again, a minimal or controlled amount of porosity of the implant is provided, such that the light transmissive and reflective properties are minimally impacted while providing adequate means for securing the implant to the surrounding tissue (which for implant 500 attachment occurs primarily via the ends 520, 524). Here again, it should be noted that the porous regions 502a may be present only on an anterior or posterior surface or may extend throughout the entire thickness of the implant 500. In addition, the upper, lower, and or entire perimeter of the implant may include porous features.

Now with reference to FIG. 16, still yet another embodiment of a bio-compatible infra-orbital implant 600 is shown having a body 602 which includes mesh regions 602a separated by a central smooth region 602b. As illustrated, mesh regions 602a (which are similar in nature to the woven graft or mesh 114 of implant 100 of FIG. 1) are disposed at a medial end 620 as well as at a lateral end 624 for the purposes of providing an attachment point for the implant. As discussed with respect to the previous embodiment, the mesh permits surrounding tissue in-growth to occur once the implant is introduced to prevent unwanted movement or shifting after it has been implanted.

Figure 17:
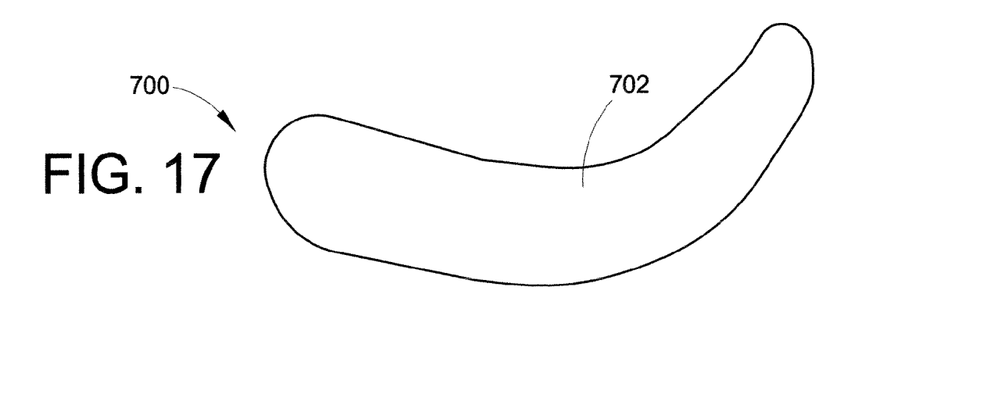
FIG. 17 is a perspective view of yet another embodiment of an infra-orbital implant having a body which includes a substantially smooth surface, according to the present invention.

Lastly, FIG. 17 illustrates still another embodiment of an implant 700 having a smooth surface over substantially the entire body 702 without any mesh or porous regions. While the implant 700 can be used individually, it may also be well suited for cases where two or more implants are used together. For example, a thinner and more pliable implant 700 could be used by itself where no infra-orbital filling is necessary. Such a thin flexible and smooth implant would thus provide the skin tone or hue correction needed to eliminate or treat dark regions below the eye while creating the least amount of disturbance to the surrounding tissue. On the other hand and by way example only, the implant 700 may be used in conjunction or in series with a second implant to address other volume related infra-orbital concerns.

It should be further noted, that any of the above discussed embodiments may include a posterior ridge. The length, width, and or thickness of the posterior ridge can be varied so as to properly accommodate the infra-orbital rim of the associated human eye. Furthermore, all of the aforementioned embodiments can be used individually or in combination with any of the other above disclosed implants. Moreover, any of the aforementioned embodiments can be secured to the periostium, muscle, skin or any other surrounding tissue using dissolvable or non-dissolvable sutures.

As is apparent from the above discussion, the present invention offers several advantages over known techniques for addressing dark circles or "sunken eyes." For one, a bio-compatible infra-orbital implant will not dissolve or be absorbed by the body unlike collagen injections and/or fat grafts. In addition, the implant is less susceptible to shifting once the implant and surrounding tissue have become interlocked via tissue in-growth. Moreover, by adjusting the placement, thickness, color, and/or reflectivity of the implant, permanent results can be achieved in correcting infra-orbital skin tone as compared to the temporary effects of chemical peels, makeup, or other topically applied substances.

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. An infra-orbital implant system for surgically altering the appearance of an infra-orbital region of an associated human eye, the implant system comprising:
   a first implant having a body made from a pliable yet resilient biocompatible material adapted for use with human tissue;
   a posterior ridge disposed on the posterior surface of the first implant between an upper and lower edge of the body of the first implant and extending in a generally posterior or rearward direction, the posterior ridge being contoured to engage an infra-orbital rim of the associated human eye and support the body of the first implant;
   wherein, the posterior ridge cooperates with the infra-orbital rim of the associated human eye to advance an anterior tissue portion overlying the first implant in a generally anterior direction when the implant is introduced beneath the skin portion of the infra-orbital region of the associated human eye.

2. The implant system of claim 1, further comprising a second implant made from a biocompatible material adapted for use with human tissue, the second implant disposed anterior to the first implant, the second implant including an anterior surface having a skin tone correction surface for correcting a skin tone of an infra-orbital skin portion of the associated human eye.

3. The implant system of claim 2, wherein the anterior surface of the second implant includes a skin tone correction surface which cooperates to lighten a skin tone of the overlying skin portion of the infra-orbital region.

4. An infra-orbital implant system for surgically altering the appearance of an infra-orbital region of an associated human eye, the implant system comprising:
- a first subcutaneous implant having a body made from a pliable yet resilient biocompatible material adapted for use with human tissue;
- a posterior ridge disposed on the posterior surface of the first implant and extending in a generally posterior or rearward direction, the posterior ridge adapted to support the first implant along an infra-orbital region of the associated human eye;
- a second subcutaneous implant made from a biocompatible material adapted for use with human tissue, the second implant disposed anterior to and spaced apart from the first implant;
- wherein the first and second implants cooperate to advance an anterior tissue portion overlying the second implant in a generally anterior direction when the first and second implants are introduced beneath the skin portion of the infra-orbital region of the associated human eye.

5. The implant system of claim 4, wherein the second implant includes an anterior surface having a skin tone correction surface for correcting a skin tone of an infra-orbital skin portion of the associated human eye overlying the second implant.

* * * * *